US00PP31860P2

(12) United States Plant Patent
Bedard

(10) Patent No.: US PP31,860 P2
(45) Date of Patent: Jun. 16, 2020

(54) FLORIBUNDA ROSE PLANT NAMED 'WEKEBTIGRAD'

(50) Latin Name: *Rosa hybrida*
Varietal Denomination: WEKebtigrad

(71) Applicant: Early Morning, LLC, Pomona, CA (US)

(72) Inventor: Christian Bedard, Rancho Cucamonga, CA (US)

(73) Assignee: Early Morning, LLC, Lawrenceburg, IN (US)

( * ) Notice: Subject to any disclaimer, the term of this patent is extended or adjusted under 35 U.S.C. 154(b) by 0 days.

(21) Appl. No.: 16/350,682

(22) Filed: Dec. 19, 2018

(51) Int. Cl.
*A01H 5/02* (2018.01)
*A01H 6/74* (2018.01)

(52) U.S. Cl.
USPC ..... Plt./141

(58) Field of Classification Search
USPC ..... Plt./141
See application file for complete search history.

(56) References Cited

U.S. PATENT DOCUMENTS

PP18,850 P2 5/2008 Carruth
PP23,476 P2 3/2013 Carruth

OTHER PUBLICATIONS www.helpmefind.com/rose/pl.php?n=112675 Retrieved from the Internet on Oct. 16, 2019 'WEKebtigrad' rose (2 pages total).*
Weeks Roses, "Award Winning", Wholesale Rose Catalog, 84 pages, 2016.
Weeks Roses, "All Dressed Up", Wholesale Rose Catalog, 86 pages, 2019.

* cited by examiner

*Primary Examiner* — Susan McCormick Ewoldt
(74) *Attorney, Agent, or Firm* — McKee, Voorhees & Sease, PLC

(57) ABSTRACT

A new variety of *Floribunda* rose suitable for garden decoration, having flowers of plum purple coloration.

1 Drawing Sheet

Classification: The present invention relates to a new *Rosa hybrida* plant.

Variety denomination: The new plant has the varietal denomination 'WEKebtigrad'.

BACKGROUND OF THE INVENTION

This invention relates to a new and distinct variety of *Floribunda* Rose. It has as its seed parent the variety known as 'WEKsmopur' (U.S. Plant Pat. No. 18,850) and as its pollen parent the variety known as 'WEKmerewby' (U.S. Plant Pat. No. 23,476).

SUMMARY OF THE INVENTION

Among the features which distinguish the new variety from other presently available and commercial rose cultivars known to the inventor are the following combinations of characteristics: its unique plum purple flower coloration, its excellent color stability throughout the life of the flowers and its numerous hairs on the rachis and petiole. The plant has an upright, compact moderately spreading growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'WEKebtigrad' may be asexually propagated by cuttings, budding and grafting. The budding and grafting successfully occurred on the plant/rootstock *Rosa hybrida* cv. 'Dr. Huey' (not patented).

COMPARISON WITH PARENTS

The new rose may be distinguished from its seed parent, 'WEKsmopur' by the following combination of characteristics: whereas 'WEKebtigrad' bears medium sized flowers (about 7.5 to about 8.7 cm. in diameter) with very double petalage (about 48 to 82 petals), 'WEKsmopur' bears larger flowers (about 8.0 to about 10.2 cm. in diameter) with significantly lesser petalage (about 25 to 48 petals). The new variety has an upright, compact moderately spreading medium height growing habit (about 90 to about 140 cm. in height), whereas the seed parent has a rounded and compact significantly shorter growing habit (about 66 to about 80 cm. in height).

The new variety may be distinguished from its pollen parent, 'WEKmerewby' by the following combination of characteristics: whereas 'WEKebtigrad' bears very double flowers (about 48 to 82 petals) of plum purple coloration, 'WEKmerewby' bears double flowers of saturate rose pink coloration with significantly lesser petalage (about 26 to 38 petals). The new variety has an upright, compact moderately spreading medium height growing habit (about 90 to about 140 cm. in height), whereas the pollen parent has an upright significantly taller growing habit (about 170 to about 190 cm. in height).

COMPARISON WITH THE CLOSEST COMMERCIALLY AVAILABLE CULTIVAR

The closest commercially available cultivar to the new variety is the seed parent 'WEKsmopur'.

BRIEF DESCRIPTION OF ILLUSTRATION

The accompanying photograph illustrates the new variety and shows the flowering thereof from bud to full bloom depicted in color as nearly correct as it is possible to make in a color illustration of the character. The branches used for the photograph came from 3 to 4 year-old rose plants of the new variety grown outdoors in Pomona, Calif. in the month of November. Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Pomona, Calif. in the month of November. Phenotypic expression may vary with environmental, cultural and climatic conditions, as well as differences in conditions of light and soil.

FLOWER

The new variety usually bears its flowers singly, sometimes in clusters of two to six or more per stem. Flowers may be borne in regular rounded clusters on strong short to medium length stems (about 13 to about 80 cm.). The cluster ranges from about 10.5 to about 13.5 cm. in diameter. Outdoors, the plant blooms abundantly and nearly continuously during the growing season. The flowers have a moderate fruity and spice fragrance.

BUD

The peduncle is about 3.0 to about 3.9 cm. in length, of average caliper (about 0.2 to about 0.3 cm. in diameter), and usually erect. It is somewhat rough, with some stipitate glands, and some hairs. Peduncle color is between 146C and 146A often moderately suffused, especially on the side exposed to the sun, with between 187B and 187A.

Before the calyx breaks, the bud is about 1.2 to about 1.6 cm. in diameter at the widest point, about 1.3 to about 1.8 cm. in length, and ovoid in shape. The surface of the bud bears between 5 to 9 foliaceous appendages with few stipitate glands and some hairs, usually with slender entire foliaceous parts extending beyond the tip of the bud about ¼ or more of its length. Bud color is between 137C and 137B.

The sepals are 5 per flower, about 2.1 to about 3.4 cm. in length and about 0.6 to about 0.8 cm. in width at the widest point. The outer surface color of the sepal is between 137C and 137B. The outer surface of the sepal is smooth and bears between 0 to 5 foliaceous appendages with few stipitate glands and some hairs. The inner surface color of the sepal is near 146C broadly bordered by near 137C. After the sepals open, the inner surface color is sometimes lightly suffused, especially on the area exposed to the sun, with between 187A and 187B. The inner surface of the sepal is covered with fine wooly tomentum; sepal margins are entire and lined with some stipitate glands and many hairs. The sepals are moderately permanent, and usually straight in shape with acute apices.

The receptacle of the flower is of medium length (about 0.4 to about 0.7 cm.) and average in caliper (about 0.5 to about 0.7 cm. in diameter). The receptacle is urn-shaped in form. Its surface is smooth with some hairs and with moderately thick fleshy walls. The receptacle color is between 146B and 137C sometimes lightly suffused, especially on the side exposed to the sun, with between 187B and 187C.

As the petals open (after the calyx breaks), the bud is about 1.6 to about 2.2 cm. in diameter at the widest point, about 1.8 to about 2.5 cm. in length, and moderately ovoid to somewhat globular in form. The color of the under surfaces of the newly opened petals is between 187A and 71A. At the point where the petal attaches, there is a small zone of between 145D and 149D. The color of the upper surfaces of the newly opened petals is between 60B and 61A at the lower third of the petal and darker than between 187A and 71A on the remaining surface of the petal. At the point where the petal attaches, there is a moderately small zone of between 2D and 150D.

BLOOM

When fully open, the bloom ranges from about 7.5 to about 8.7 cm. in diameter. Petalage is very double with about 48 to 82 petals and about 4 to 8 petaloids irregularly arranged. When partially open, the bloom form is somewhat high centered to cupped, and the petals are moderately tightly spiraled to cupped with petal edges somewhat reflexed outward. When fully open, the bloom form is more cupped, and the petals are somewhat loosely cupped with petal edges somewhat reflexed outward.

PETALS

The substance of the petals is heavy and of medium to somewhat thick thickness, with upper surfaces moderately velvety and under surfaces slightly shiny. The petals are about 3.1 to about 4.8 cm. in length and about 2.0 to about 5.1 cm. in width at the widest point. Petal margins are entire.

The outer petals are moderately rounded to somewhat obovate in shape with rounded apices.

The inner petals are oblanceolate to somewhat obovate in shape with rounded apices.

Petaloids are about 0.9 to about 3.1 cm. in length and about 0.5 to about 2.2 cm. in width at the widest point. Petaloids are irregularly shaped moderately oblanceolate to somewhat obovate to subulate with rounded apices.

NEWLY OPENED FLOWER

The under surface color of the outer, intermediate and inner petals is between 71A and 64A. At the point where the petal attaches, there is a small zone of between 155A and 155B. The upper surface color of the outer, intermediate and inner petals is between 74A and 78A at the lower third of the petal and between 79B and 71A on the remaining surface of the petal. At the point where the petal attaches, there is a somewhat large zone of between 155A and 155B.

The under and upper surface colors of the petaloids are similar in coloration to the upper and under surfaces of the intermediate and inner petals.

The general tonality of the newly opened flower is between 74A and 78A at the lower third of the petal and between 79B and 71A on the remaining surface of the petal.

THREE-DAY-OLD FLOWER

The under surface color of the outer, intermediate and inner petals is between 61A and 64A. At the point where the petal attaches, there is a small zone of between 155A and 155B. The upper surface color of the outer, intermediate and inner petals is between 74A and 78A at the lower third of the petal and between 79B and 71A on the remaining surface of the petal. At the point where the petal attaches, there is a somewhat large zone of between 155A and 155B.

The under and upper surface colors of the petaloids are similar in coloration to the upper and under surfaces of the intermediate and inner petals.

The general tonality of the three-day-old flower is between 74A and 78A at the lower third of the petal and between 79B and 71A on the remaining surface of the petal.

On the spent bloom, the petals usually drop off cleanly.

In November in Pomona, Calif., blooms on the bush growing outdoors generally last about four to five days. Cut roses from plants grown outdoors and kept at normal indoor living temperatures generally last about four to five days.

MALE REPRODUCTIVE ORGANS

Stamens are average in number (average about 50) and are arranged regularly about the pistils; a few are mixed with petaloids. The filaments are of somewhat short to medium length (about 0.4 to about 0.9 cm.) most with anthers. Filaments are between 1D and 154D in color sometimes lightly suffused with between 53B and 53C. The anthers are somewhat small for the class and all open approximately at the same time. Anther color when immature is near 20A on the external part and near 11D on the internal part. Anther color at maturity is near 164B on the external part and near 200A on the internal part. Pollen is moderate and between 18B and 19C in color.

FEMALE REPRODUCTIVE ORGANS

Pistils vary in number (average about 40). The styles are moderately even, average to somewhat long in length (about 0.6 to about 0.8 cm.), thin in caliper, and loosely bunched to somewhat separated. Stigma color is near 16C. Style color is between 4D and 2D often moderately suffused with between 60A and 60B. Ovaries are usually all enclosed in the calyx.

The ovaries are of small size and between 158B and 158C in color.

Hips have not been observed on this variety when grown in Pomona, Calif.

FOLIAGE

The compound leaves are usually comprised of three to seven leaflets and are borne abundantly. The five-leaflet leaves are about 9.0 to about 14.4 cm. in length and about 7.1 to about 11.1 cm. in width at the widest point, moderately leathery to somewhat crisp in texture on both sides, and glossy in finish on the upper side and matte in finish on the under side. The leaves have a pinnate venation pattern. The terminal leaflets are about 3.8 to about 7.2 cm. in length and about 2.4 to about 5.2 cm. in width at the widest point, shaped ovate to somewhat oval with acute to somewhat acuminate apices and rounded bases. Their margins are usually simply serrate.

The upper surface color of the mature leaf is between 137A and 139A. The under surface color of the mature leaf is between 147B and 146B. The under and upper colors of the leaf veins on the mature leaf are similar in coloration to the upper and under surfaces colors of the mature leaf. The upper surface color of the young leaf is between 137A and 137B, often heavily suffused with between 187B and 187A. The under surface color of the young leaf is near 146B, often heavily suffused with between 187B and 187A. The under and upper colors of the leaf veins on the young leaf are similar in coloration to the upper and under surfaces colors of the young leaf The rachis is about 4.1 to about 7.2 cm. in length, about 0.1 to about 0.2 cm in width at the widest point, and smooth. The upper side is deeply grooved with numerous hairs and few stipitate glands on the edges of the grooves. The under side of the rachis is smooth with numerous hairs and few stipitate glands. The rachis color is near 146C on the under side and near 137B on the upper side, often moderately suffused on the young leaves with between 187B and 187C.

The stipules are about 1.2 to about 2.0 cm. in length and of medium to somewhat wide width (about 0.5 to about 0.8 cm.) with moderately long straight points that usually turn out at an angle of more than 45 degrees. The under and upper surface color of the stipule is between 137A and 137B. The upper and under surfaces of the stipules are smooth in texture.

The petiole is somewhat light to average in caliper and smooth. The upper side is deeply grooved with numerous hairs and few stipitate glands on the edges of the grooves. The under side of the petiole is smooth with numerous hairs and few stipitate glands. The petiole is about 0.3 to about 1.3 cm. in length and about 0.1 to about 0.2 cm in width at the widest point. The petiole color is near 146C on the under side and near 137B on the upper side, often moderately suffused on the young leaves with between 187B and 187C.

The plant displays an above average degree of resistance to powdery mildew (*Sphaerotheca pannosa*), downy mildew (*Peronospora sparsa*), and rust (*Phragmidium* sp.) as compared to other commercial varieties grown under comparable conditions in Pomona, Calif. The plant's winter hardiness and drought/heat tolerance are yet to be determined.

GROWTH

The plant has an upright, compact moderately spreading medium height growing habit (about 90 to about 140 cm. in height and about 85 to about 115 cm. spread at the widest point), with moderately full branching. It displays moderately vigorous growth and the canes are of medium to somewhat heavy caliper for the class (about 1.2 to about 3.4 cm. in diameter at the widest point).

The color of the major stems is between 147B and 146B. The major stems are rough in texture and they bear few large prickles that are about 0.8 to about 1.1 cm. in length. The large prickles are moderately angled to somewhat hooked downward with a medium length broad oval base; prickle color is between 166D and 165B sometimes moderately suffused with between 201C and 201D. The major stem bears very few small prickles of similar shape and coloration.

The color of the branches is between 146A and 146B often moderately suffused with between 187B and 183A. The branches are rough in texture and they bear few large prickles which are of similar shape to the large prickles on the major stems. The prickles are about 0.5 to about 0.7 cm. in length. Prickle color is between 165B and 164A. The branches bear few small prickles of similar shape and coloration.

The color of the new shoots is between 146A and 146B often moderately suffused with between 187A and 187B.

The new shoots are rough in texture and they bear few large prickles which are of similar size and shape to the large prickles on the branches; prickle color is between 152C and 152D often moderately suffused with between 187B and 187C. The shoots bear few small prickles of similar shape and coloration.

I claim:

1. A new and distinct *Floribunda* rose plant of the variety substantially as described and illustrated herein.

* * * * *

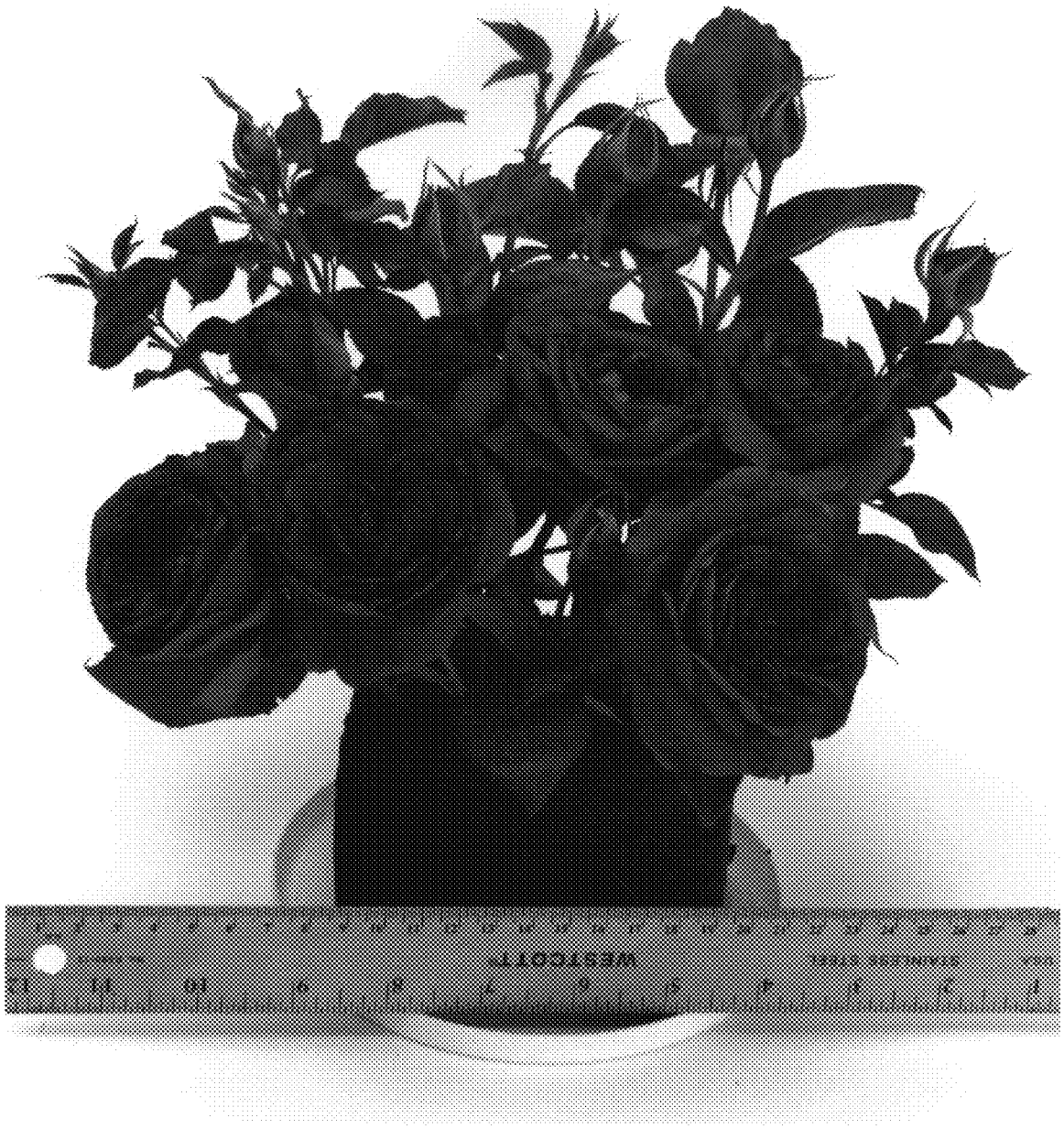
WESTCOTT